US009044511B2

(12) United States Patent
Rauo

(10) Patent No.: US 9,044,511 B2
(45) Date of Patent: Jun. 2, 2015

(54) PEPTIDE

(75) Inventor: Jaran Rauo, Tromso (NO)

(73) Assignee: Marealis AS (NO)

( * ) Notice: Subject to any disclaimer, the term of this patent is extended or adjusted under 35 U.S.C. 154(b) by 0 days.

(21) Appl. No.: 13/880,883

(22) PCT Filed: Jul. 13, 2011

(86) PCT No.: PCT/GB2011/051314
§ 371 (c)(1),
(2), (4) Date: Jul. 3, 2013

(87) PCT Pub. No.: WO2012/056205
PCT Pub. Date: May 3, 2012

(65) Prior Publication Data
US 2013/0281358 A1 Oct. 24, 2013

(30) Foreign Application Priority Data

Oct. 26, 2010 (GB) .................................. 1018125.3

(51) Int. Cl.
| A23L 1/305 | (2006.01) |
| A61K 38/06 | (2006.01) |
| A61K 38/55 | (2006.01) |
| C07K 5/08 | (2006.01) |
| C07K 5/087 | (2006.01) |
| C07K 5/107 | (2006.01) |
| A61P 9/12 | (2006.01) |
| A61K 45/06 | (2006.01) |

(52) U.S. Cl.
CPC ............... *A61K 45/06* (2013.01); *A61K 35/612* (2013.01); *A61K 38/06* (2013.01); *C07K 5/0812* (2013.01); *A23L 1/3053* (2013.01)

(58) Field of Classification Search
CPC ..... A61K 38/06; A61K 35/612; A61K 45/06; A23L 1/3053; C07K 5/0812
See application file for complete search history.

(56) References Cited

U.S. PATENT DOCUMENTS

| 4,455,303 A * | 6/1984 | Burton .......................... 514/15.8 |
| 5,545,719 A | 8/1996 | Shashoua |
| 2009/0253641 A1* | 10/2009 | Neufer et al. .................... 514/18 |
| 2012/0149640 A1 | 6/2012 | Carelli et al. |

FOREIGN PATENT DOCUMENTS

| WO | WO-2004/056851 A1 | 7/2004 |
| WO | WO-2005/001023 A2 | 1/2005 |
| WO | WO 2005007090 A2 * | 1/2005 | ............. C12N 15/00 |
| WO | WO-2006/119527 A2 | 11/2006 |
| WO | WO-2007/004869 A2 | 1/2007 |
| WO | WO-2007/117444 A1 | 10/2007 |
| WO | WO 2008050161 A2 * | 5/2008 | ............. C07K 5/062 |
| WO | WO-2010/106294 A1 | 9/2010 |
| WO | WO-2011/144940 A1 | 11/2011 |

OTHER PUBLICATIONS

WebMD, Heart Disease and ACE inhibitors, http://www.webmd.com/heart-disease/guide/medicine-ace-inhibitors, accessed on Dec. 18, 2013.*
Eva Lonn, Angiotensin-converting Enzyme Inhibitors and Angiotensin Receptor Blockers in Atherosclerosis Current Atherosclerosis Reports, 2002, 4:363-372.*
Uniprot Protein Database, Accession No. D0KSW8 (D0KSW8_SULS9), DNA Polymerase, pp. 1-4, Accessed on Jul. 10, 2014.*
Uniprot Protein Database, Accession No. Q4TVV4 (Q4TVV4_PIG), Gastrin related protein, pp. 1-3m accessed on Jul. 10, 2014.*
"International Application Serial No. PCT/GB2011/051314, International Search Report mailed Feb. 23, 2012", 5 pgs.
"International Application Serial No. PCT/GB2011/051314, Written Opinion mailed Feb. 23, 2012", 10 pgs.
Bougatef, A., et al., "Angiotensin I-converting enzyme (ACE) inhibitory activities of sardinelle (*Sardinella aurita*) by-products proteinhydrolysates obtained by treatment with microbial and visceral fish serine proteases", *Food Chemistry*, 111(2), (2008), 350-356.
Cheung, I. W. Y., et al., "Angiotensin-I-converting enzyme inhibitory activity and bitterness of enzymatically-produced hydrolysates of shrimp (*Pandalopsis dispar*) processing byproducts investigated by Taguchi design", *Food Chemistry*, 122(4), (2010), 1003-1012.
Gildberg, A., et al., "Angiotensin I-converting enzyme inhibitory activityin a hydrolysate of proteins from Northern shrimp (*Pandalus borealis*) and identification of two novel inhibitory tri-peptides", *Process Biochemistry*, 46(11), (2011), 2205-2209.
Li, C.-H., et al., "Latent Production of Angiotensin I-Converting Enzyme Inhibitors from Buckwheat Protein", *Journal of Peptide Science*, 8(6), (2002), 267-274.
Torruco-Uro, J. G., et al., "Antihypertensive Peptides, an Alternative for Treatment of Natural Origin: A Review", *Ciencia Y Tecnologia Alimentaria*, 6(2), (2008), 158-168.
Vercruysse, L., et al.. "ACE Inhibitory Peptides Derived from Enzymatic Hydrolysates of Animal Muscle Protein: A Review", *Journal of Agricultural and Food Chemistry*, 53(21), (2005), 8106-8115.
Wu, J., et al., "Structural Requirements of Angiotensin I-Converting Enzyme Inhibitory Peptides: Quantitative Structure-Activity Relationship Study of Di- and Tripeptides", *Journal of Agricultural and Food Chemistry*, 54(3), (2006), 732-738.
Balti, R., et al., "Three novel angiotensin I-converting enzyme (ACE) inhibitory peptides from cuttlefish (*Sepia officinalis*) using digestive proteases", *Food Research International*, 43, (2010). Cushman, D. W., et al., "Concentrations of angiotensin-converting enzyme in tissues of the rat", Biochemica et Biophysica Acta, 250, (1971), 261-265.
Dragnes, B. T., et al., "Utilisation of fish industry residuals: Screening the taurine concentration and angitensin converting enzyme inhibition potential in cod and salmon", *J. Food Comp. Analy.* 22, (2009), 714-717.

(Continued)

*Primary Examiner* — James H Alstrum Acevedo
*Assistant Examiner* — Erinne Dabkowski
(74) *Attorney, Agent, or Firm* — Schwegman Lundberg & Woessner, P.A.

(57) ABSTRACT

The invention provides a peptide comprising or consisting of FSY and variants thereof, particularly comprising of consisting of the sequence FTY, nucleic acids encoding said peptides and pharmaceutical and nutraceutical compositions comprising said peptide(s) and/or nucleic acids. Also provided is the use of such a peptide in therapy and in vitro methods of ACE-inhibition.

4 Claims, No Drawings

(56) References Cited

OTHER PUBLICATIONS

Erdmann, K., et al., "The possible roles of food-derived bioactive peptides in reducing the risk of cardiovascular disease", *Journal of Nutritional Biochemistry*, 19, (2008), 643-654.

Fujita, H., et al., "LKPNM: a prodrug-type ACE-inhibitory peptide derived from fish protein", *Immunopharmacology*, 44, (1999), 123-127.

Harnedy, P. A., et al., "Bioactive peptides from marine processing waste and shellfish: A review", *Journal of Functional Foods*, 4, (2012), 6-24.

Hernandez-Ledesma, B., et al., "Antihypertensive peptides: Production, bioavailability and incorporation into foods", *Advances in Colloid and Interface Science*, 165, (2011), 23-35.

Kawasaki, T., et al., "Antihypertensive effect of Valyl-Tyrosine, a short chain peptide derived from sardine muscle hydrolyzate, on mild hypertensive subjects", *Journal of Human Hypertension*, 14, (2000), 519-523.

Li, G.-H., et al., "Angiotensin I-converting enzyme inhibitory peptides derived from food proteins and their physiological and pharmacological effects", *Nutrition Research*, 24, (2004), 469-489.

Matsui, T., et al., "Absorption of Val-Tyr with in Vitro Angiotensin I-Converting Enzyme Inhibitory Activity into the Circulating Blood System of Mild Hypertensive Subjects", *Biol. Pharm. Bull.*, 25(9), (2002), 1228-1230.

Matsui, T., et al., "Antihypertensive peptides from natural resources", *In: Lead Molecules from Natural Products*, M. T.H. Khan and A. Ather, Editors, Elsevier B.V., (2006), 255-271.

Miguel, M., et al., "ACE-inhibitory and antihypertensive properties of a bovine casein hydrolysate", *Food Chemistry*, 112, (2009), 211-214.

Murray, B. A., et al., "Angiotensin Converting Enzyme Inhibitory Peptides Derived from Food Proteins: Biochemistry, Bioactivity Production", *Current Pharmaceutical Design*, 13, (2007), 773-791.

Nii, Y., "Determination of Antihypertensive Peptides from an Izumi Shrimp Hydrolysate", *Biosci. Biotechnol. Biochem.*, 72(3) (2008), 861-864.

Vermeirssen, V., et al., "Optimisation and validation of an angiotensin-converting enzyme inhibition assay for the screening of bioactive peptides", *J. Biochem. Biophys. Methods*, 51, (2002), 75-87.

Wilson, J., et al., "Angiotensin-I-converting enzyme and prolyl endopeptidase inhibitory peptides from natural sources with a focus on marine processing by-products", *Food Chemistry*, 129, (2011), 235-244.

\* cited by examiner

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: A synthetic peptide

<400> SEQUENCE: 1

Leu Val Ala Lys
1

<210> SEQ ID NO 2
<211> LENGTH: 4
<212> TYPE: PRT
<213> ORGANISM: Artificial Sequence
<220> FEATURE:
<223> OTHER INFORMATION: A synthetic peptide

<400> SEQUENCE: 2

Leu Val Ala His
1

<210> SEQ ID NO 3
<211> LENGTH: 4
<212> TYPE: PRT
<213> ORGANISM: Artificial Sequence
<220> FEATURE:
<223> OTHER INFORMATION: A synthetic peptide

<400> SEQUENCE: 3

Leu Leu Thr Lys
1
```

```
<210> SEQ ID NO 4
<211> LENGTH: 4
<212> TYPE: PRT
<213> ORGANISM: Artificial Sequence
<220> FEATURE:
<223> OTHER INFORMATION: A synthetic peptide

<400> SEQUENCE: 4

Ala Leu Pro His
1

<210> SEQ ID NO 5
<211> LENGTH: 4
<212> TYPE: PRT
<213> ORGANISM: Artificial  Sequence
<220> FEATURE:
<223> OTHER INFORMATION: A synthetic peptide

<400> SEQUENCE: 5

Leu Leu Leu Lys
1

<210> SEQ ID NO 6
<211> LENGTH: 4
<212> TYPE: PRT
<213> ORGANISM: Artificial Sequence
<220> FEATURE:
<223> OTHER INFORMATION: A synthetic peptide

<400> SEQUENCE: 6

Leu Asn Pro Lys
1

<210> SEQ ID NO 7
<211> LENGTH: 4
<212> TYPE: PRT
<213> ORGANISM: Artificial Sequence
<220> FEATURE:
<223> OTHER INFORMATION: A synthetic peptide

<400> SEQUENCE: 7

Val Leu Ala His
1
```

PEPTIDE

RELATED APPLCIATION

This application is a national stage application under 35 U.S.C. §371 of PCT/GB2011/051314, filed Jul. 13, 2011 and published as WO 2012/056205 A1 on May 3, 2012, which claimed priority to United Kingdom Patent Application Ser. No. 1018125.3, filed Oct. 26, 2010; which applications and publication are incorporated herein by reference in their entirety.

FIELD OF THE INVENTION

The present invention concerns peptides having ACE-inhibitory properties, variants thereof, compositions comprising the same and uses thereof, particularly medical uses such as the treatment of hypertension.

BACKGROUND

Hypertension is one of the risk factors for strokes, heart attacks, heart failure and arterial aneurysm, and is a leading cause of chronic renal failure. Even moderate elevation of arterial blood pressure leads to shortened life expectancy.

Hypertension may be treated by targeting Angiotensin I-converting enzyme (ACE). ACE is an enzyme that participates in the body's renin-angiotensin system (RAS). It is an exopeptidase which catalyzes the conversion of the decapeptide angiotensin I to the octapeptide angiotensin II. Angiotensin II causes blood vessels to constrict, and drives blood pressure up. It also stimulates the release of aldosterone from the adrenal cortex. Aldosterone promotes sodium retention in the distal nephron, in the kidney, which also drives blood pressure up.

ACE inhibitors are inter alia used for controlling blood pressure, treating heart failure, preventing strokes, and preventing kidney damage in people with hypertension or diabetes. They also improve survival after heart attacks. Commonly used ACE inhibitors include benazepril (Lotensin®), captopril (Capoten®), enalapril (Vasotec®), fosinopril (Monopril®), lisinopril (Prinivil®, Zestril®), moexipril (Univasc®), perindopril (Aceon®), quinapril (Accupril®), ramipril (Altace®), and trandolapril (Mavik®). These drugs often have undesired side effects and/or they are not effective enough, so there remains a need for further ACE inhibitors.

A number of different peptides have been found to have ACE-inhibitory activity (Vercruysse et al. September 2005, Journal of Agricultural and Food Chemistry A-J) and there remains a need to further peptides having ACE-inhibitory activity.

DESCRIPTION OF THE INVENTION

The present inventors have identified a peptide which has particularly good ACE-inhibitory activity. The peptide has the sequence FSY, wherein F stands for phenylalanine, also denoted Phe, S stands for serine, also denoted Ser, and Y stands for tyrosine, also denoted Tyr. Thus, the present invention provides in one aspect a peptide comprising or consisting of FSY.

The present inventors have also determined that a variant of the above peptide, having the sequence FTY, also has particularly good ACE-inhibitory activity. T stands for threonine, also denoted Thr. Thus, the present invention provides in a further aspect a peptide comprising or consisting of FTY.

"FSY/FTY" is used herein to indicate that the peptide may have the sequence FSY or FTY.

The peptide may comprise at least 3, 4, 5, 6, 7, 8, 9, 10,12, 14, 16, 18, 20, 30, 40 or 50 amino acids, and preferably no more than 50, 40, 30, 25, 20, 19, 18, 17, 16, 15, 14, 13, 12, 11, 10, 9, 8, 7, 6, 5 or 4 amino acids, e.g. 3-25, 3-15, 3-10, 3-8, 3-7, 3-6, 3-5 or 3-4 amino acids, preferably it may consist of 4, 5, 6, 7, 8, 9 10, 12, 14, 16, 18 or 20 amino acids, most preferably it consists of 3 amino acids. By "consisting of" a number of amino acids is meant that the number of amino acids present does not exceed the recited number, but this expression does not exclude the possibility that the peptide includes a further non-peptide moiety. For example, the peptide may be phosphorylated or it may include a C-terminal cap, as discussed below.

Thus, the peptide has the core amino acid sequence FSY or FTY. The term "core amino acid sequence" as used herein refers to a sequence of amino acids that may begin at the N-terminus of a peptide, may be an internal sequence in a peptide, may end at the C-terminus of a peptide, or may begin at the N-terminus of a peptide and end at the C-terminus of a peptide. Amino acids at the N- and/or C-terminal side of the core sequence are referred to as "flanking" amino acids.

The FSY/FTY peptide may be recombinant, i.e. it may have been expressed from a heterologous gene in a host cell such as *E. coli* and purified therefrom. It may be obtained from a non-recombinant source, e.g. isolated from a sample of an animal or plant that naturally produces the peptide. It may be obtained by enzymatically or chemically breaking down, e.g. hydrolysing, a protein comprising the FSY/FTY sequence. Standard methods of peptide synthesis, e.g. solid phase synthesis, may be used to synthesise the peptide, Fmoc or Boc solid phase synthesis being preferred.

Also provided is thus a method of producing an isolated FSY/FTY peptide. Said method may involve any of the methods mentioned above. Preferably, said method involves a step of hydrolysing a proteinaceous composition to yield a hydrolysate and isolating the FSY/FTY peptide from the hydrolysate.

Also provided is a method of producing a composition comprising an FSY/FTY peptide, said method comprising hydrolysing a protein comprising the FSY/FTY motif to yield a composition comprising an FSY/FTY peptide.

Unless stated otherwise, any of the production methods mentioned herein may be carried out on a pure protein or on a mixture of proteins. The mixture of proteins may, for example, be shrimp processing waste comprising heads, tails and/or shells of shrimp, preferably *Pandalus borealis*.

Optionally, the peptide may include 1, 2 or 3 conservative substitution of the FSY/FTY amino acid sequence, preferably no more than 1. Ser is a polar neutral amino acid, so substituting Cys, Met, Thr, Asn or Gln for Ser represents a conservative substitution. Phe and Tyr are aromatic amino acids, so they may each independently be substituted for Phe, Trp or Tyr. Thus, peptides having a core sequence selected from FTY, YSY, YSF, FCY, FMY, FNY and the like are also contemplated.

Optionally, the peptide may include a non-genetically coded amino acid in the core and/or flanking sequence, although it is preferred that the core sequence does not comprise any non-genetically coded amino acids. By "non-genetically coded amino acid" is meant an amino acid which differs from the 20 genetically coded amino acids by its side chain. Thus, this term is used herein to refer to the side chain, and is not used herein to distinguish between L and D amino acids. Examples of non-genetic amino acids include 3-iodo-L-tyrosine, azidoalanine, azidohomoalanine and norleucine.

It is well known that the stability of peptides may be improved by so called end-cappings, i.e. chemical modifications of the N- and C-terminal amino acids. Typical end-cappings include amidation of the C-terminus and acetylation or deamination of the N-terminus. Thus, in some embodiments, the peptide disclosed herein has a modified C-terminus and/or a modified N-terminus, preferably an amidated C-terminus and/or an acetylated or deaminated N-terminus.

The L-configuration is preferred, so preferably all of the amino acids of the peptide are in the L configuration, but the peptide may comprise one or more amino acids in the D configuration. Optionally, more than half or all of the amino acids are in the D configuration. Optionally, the core sequence only includes L-amino acids and the flanking sequence(s) include one or more D-amino acids, or vice versa.

Optionally, one or more of the amino acids of the core and/or flanking sequence may be glycosylated. Optionally, one or more of the amino acids of the core and/or flanking sequence may be phosphorylated.

The amino acids which make up the peptide will typically be linked via peptidic bonds, preferably alpha-peptidic bonds. These are a type of amide bond. However, one or more of the amino acids may be linked by non-peptidic bonds.

Preferably, the peptide is linear, but it may optionally be circular or branched.

The term "FSY/FTY peptide" is conveniently used herein to refer to a peptide as defined above, i.e. a peptide consisting of or comprising the sequence FSY/FTY which may optionally include one or more of he modifications discussed herein.

The FSY peptide has ACE-inhibitory activity. As shown in Example 1, the inventors have provided an FSY peptide having an $IC_{50}$ with respect to ACE inhibition of about 4 μM (average of several measurements). Typical measurements using the method of Dragnes et al. showed an $IC_{50}$ with respect to ACE inhibition of about 2.2 μM. The method of Vermeirssen measured an $IC_{50}$ with respect to ACE inhibition of about 7.7 μM.

The FTY peptide also has ACE-inhibitory activity. As shown in Example 2, the inventors have provided an FTY peptide having an $IC_{50}$ with respect to ACE inhibition of about 59 μM (using the method of Dragnes et al.) The method of Vermeirssen measured an $IC_{50}$ with respect to ACE inhibition of about 274 μM.

Thus, with respect to ACE inhibition the $IC_{50}$ of the peptide is preferably less than 400, 300, 200, 190, 180, 170, 100, 80, 60, 40, 30 or 20 μM, most preferably less than 18, 16, 14, 12, 10, 8, 7, 6, 5, 4, 3, or 2 μM, e.g. about 4 μM, preferably about 3, 2, 1.7 or 1 μM. For example, the $IC_{50}$ of the peptide may be about 1-20, 1-10, 1-6, 1-4 or 1-2 μM.

ACE-inhibition has various therapeutic applications as discussed below. In all of the therapeutic applications contemplated herein, the FSY/FTY inhibits ACE activity. The FSY/FTY peptide may thus be used to treat any condition characterised by aberrant ACE activity. By "aberrant" ACE activity is meant that the ACE activity is too high, i.e. higher than in a healthy subject. Examples of such conditions are prehypertension and hypertension. Alternatively viewed, the FSY/FTY peptide may be used to treat any subject who can benefit from ACE inhibition, e.g. a subject having, or being at risk of developing, prehypertension or hypertension.

It should be understood that in the therapeutic applications disclosed herein, the FSY/FTY peptide is used in an ACE-inhibitory effective amount.

Thus, in a further aspect there is provided a pharmaceutical composition comprising an FSY/FTY peptide together with a pharmaceutically acceptable carrier or excipient.

In a further aspect there is provided an FSY/FTY peptide for use in therapy, preferably for use in lowering blood pressure and/or preventing or reducing the development or progression of prehypertension or hypertension.

There is also provided a method of inhibiting ACE-activity, comprising administering to a subject in need thereof an ACE-inhibitory effective amount of an FSY/FTY peptide disclosed herein.

There is also provided a method of treating or preventing the development or progression of prehypertension or hypertension, comprising administering to a subject in need thereof a pharmaceutically effective amount of an FSY/FTY peptide disclosed herein.

ACE-inhibitory activity may be assayed using known methods, for example based on the method reported by Cushman and Cheung (1971) by measuring the end product hippuric acid (HA) from the enzymatic reaction between ACE (Sigma A 6778) and the substrate HHL (Sigma H 1635). (CUSHMAN, D. W. & CHEUNG, H. S. (1971). Concentrations of Angiotensin-Converting Enzyme in Tissues of Rat. Biochimica Et Biophysica Acta 250(1), 261-265 and Dragnes et al. J Food Composition and Analysis 2009; 22: 714-17). A different suitable assay is disclosed by Vermeirssen et al. (2002), J. Biochem Biophys. Methods 51 (2002), pages 75-87, which is incorporated herein by reference. Briefly, this is a spectrophotometric method in which ACE inhibition is measured using the substrate furanacryloyl-Phe-Gly-Gly and rabbit lung acetone extract as the ACE source. The $IC_{50}$ may be determined. $IC_{50}$ is defined as the concentration at which activity is inhibited by 50%.

Inhibition of ACE in vivo typically has antihypertensive effects, so the in vivo effect of the FSY peptide may be assayed using spontaneously hypertensive rats (SHRs). SHRs are a widely accepted animal model for hypertension and suitable strains are commercially bred. SHRs have normal blood pressure at a young age, but as they age, they develop spontaneous and long-lasting hypertension, particularly systolic blood pressure over 150 mmHg. The FSY/FTY peptide may be tested for its ability to inhibit hypertension in these rats. The inhibition may be complete, i.e. preventing the development of any hypertension, or partial, causing the hypertension to be less severe in FSY/FTY peptide-treated rats compared to untreated rats. The in vivo antihypertensive effects of the FSY/FTY peptide may also be tested in other animals, e.g. using subjects suffering from hypertension or by testing the ability of the FSY/FTY peptide to counter-act the hypertensive effects of one or more blood-pressure raising agents.

Blood pressure is generally measured in 'millimeters of mercury' (mmHg) and it is expressed in terms of systolic pressure and diastolic pressure. Systolic pressure is peak pressure in the arteries, which occurs near the end of the cardiac cycle when the ventricles are contracting. Diastolic pressure is minimum pressure in the arteries, which occurs near the beginning of the cardiac cycle when the ventricles are filled with blood. An example of normal measured values for a resting, healthy adult human is 90-120 mmHg systolic and 60-80 mmHg diastolic, e.g. 110 mmHg systolic and 70 diastolic (written as 110/70 mmHg).

For humans, "high blood pressure" is typically defined as a blood pressure that is 140/90 mmHg or above substantially each time it is taken. That is, it is "sustained" at 140/90 mmHg or above. However, "high blood pressure" also includes a high systolic pressure combined with a normal diastolic pressure, or a high diastolic pressure combined with a normal systolic pressure. Thus, "high blood pressure" or "hypertension" as used herein means a systolic pressure of 140 mmHg or above and/or a diastolic pressure of 90 mmHg or above. A subject having hypertension may thus have a systolic pressure of at least 140, 145, 150, 155, 160, 165 or 170 mmHg and/or a diastolic pressure of at least 90, 95, 100, 105, 110, 115 or 120 mmHg.

Blood pressures between 120/80 and 139/89 are referred to herein as "prehypertension", which is indicative of human subjects having an increased risk of developing hypertension.

The values for normal or high blood pressure of other animals are known in the art.

The FSY/FTY peptide or composition comprising an FSY/FTY peptide may be used in the treatment or prevention of prehypertension or hypertension. It may therefore be particularly useful in the treatment or prevention of a disorder selected from a coronary artery disease (CAD) or a coronary heart disease (CHD), such as angina pectoris, hypertension, atherosclerosis, stroke, myocardial infarction, cerebral infarction, and restenosis following angioplasty, arrhythmia, tachyarrythmia, congestive heart failure (CHF), aortic valve regurgitation; dyslipidemia; dyslipoproteinemia; vascular diseases associated with diabetes, such as diabetic nephropathy, diabetic neuropathy, microalbumia and diabetic retinopathy; renal diseases, in particular acute and chronic renal failure. As mentioned above, in all of these therapeutic applications the FSY/FTY peptide is used to inhibit ACE activity.

The FSY/FTY peptide is preferably capable of lowering the systolic and/or diastolic blood pressure by at least about 1, 2, 3 or 4 mmHg, more preferably at least about 5, 6, 7 or 8 mmHg, preferably by at least about 9, 10, 11, 12, 13, 14 or 15 mmHg, for example about 1-20, 2-15, 3-10 or 5-10 mmHg after administration for at least 1, 2, 3, 4, 5, 6, 7, 10, 14, 21 or 28 days, preferably after about 7 days.

In some embodiments, the FSY/FTY peptide inhibits the systolic and/or diastolic blood pressure from increasing. This inhibition may be complete, causing the systolic and/or diastolic blood pressure to remain stable, or it may be partial, slowing down any increase in systolic and/or diastolic blood pressure. Such inhibition may be assessed for example by comparing any change in the systolic and/or diastolic blood pressure over a period prior to administration of the FSY/FTY peptide to the change over a period during administration of the FSY/FTY peptide.

It may also be assessed by comparing any change in the systolic and/or diastolic blood pressure of subjects receiving the FSY/FTY peptide to control subjects who receive a placebo or no treatment.

Any mammal may be treated, for example humans and any livestock, domestic or laboratory animal. Specific examples include mice, rats, pigs, cats, dogs, sheep, rabbits, cows and monkeys. Preferably, however, the mammal is a human.

The terms "therapy" or "treatment" as used herein include prophylactic therapy, which may result in the prevention of disease, as well a therapeutic treatment of an established disorder. The terms "therapy" and "treatment" include combating or cure of disease but also include the controlling, reduction or alleviation of disease or one or more of the symptoms associated therewith.

An "effective amount" as used herein can refer to a therapeutically effective amount or a prophylactically effective amount depending on the nature of the treatment. A therapeutically effective amount can be considered to be an amount necessary (at appropriate dosages and administration regimes) to achieve the desired therapeutic result. A prophylactically effective amount can be considered to be an amount necessary (at appropriate dosages and administration regimes) to achieve the desired prophylactic result. The amounts are likely to vary depending on the weight, age and sex of the patient as well as the severity of the disease. Advantageously, the FSY/FTY peptide is used in an ACE-inhibitory effective amount, which is preferably effective in the prophylactic and/or therapeutic treatment of any of the conditions listed herein.

In a further aspect, the present invention provides a nutraceutical composition comprising an FSY/FTY peptide and optionally further ingredients. The term "nutraceutical" as used herein denotes a product that may provide health benefits in addition to nutritional benefits. The nutraceutical of the present invention has ACE-inhibitory activity. Thus, the nutraceutical may preferably lower blood pressure and/or prevent or reduce the development or progression of high blood pressure. Alternatively or in addition, it may stimulate the immune response and/or stimulate growth, particularly when administered to animals as animal feed.

The nutraceutical composition may be formulated as a supplement, e.g. it may be a solid formulation such as capsules, tablets or a powder, or a liquid formulation, such as solutions or suspensions. It may also be formulated as a food for humans, or a feed for non-human animals, by combining or incorporating it with one or more further edible materials. The edible materials may be liquid or solid.

Food products which may be formulated to comprise a peptide or nutraceutical composition of the present invention include but are not limited to instant powder products, food bars such as candy bars or protein bars, meat and meat analogue products, fish and fish analogue products, breakfast cereals, vegetable fat spreads, mayonnaise, dairy products, soy milk products, pasta, noodles, baked goods such as bread, pastry, cakes and biscuits, ready meals, infant formula and baby food.

Suitable examples of dairy products include butter, cheese, ice cream, yogurt, whipping cream, sour cream and cottage cheese. Examples of meat products include, but are not limited to, processed meat such as pate, ham, spam, sausage and whole muscle meat. The meat analogue may be a textured vegetable, fungal or dairy protein that mimics meat in texture such as quorn or tofu.

Non-limiting examples of protein fortified liquid beverages which may be formulated to comprise a peptide or nutraceutical composition according to the invention include carbonated fortified soft drinks, beer, fruit juices, fruit-flavored drinks, vegetable drinks, sports drinks, soy milk drinks, rice milk drinks, infant formula, milk, flavoured milk drinks, goat milk, liquid yogurt, buttermilk or combinations thereof.

The feed which may be formulated to comprise a peptide or nutraceutical composition according to the invention may be any animal feed, including pet food. The feed may be in a dry or moist form.

Typical components of food, feeds or nutraceutical compositions, in addition to the FSY/FTY peptide, may include crude protein, crude fat, carbohydrates, polysaccharides, starch, crude fibres, ash, minerals, trace elements, vitamins, fatty acids, proteins, peptides (other than an FSY/FTY peptide), amino acids, herbs, lipids, antioxidants, carotenoids, tocopherols, tocotrienols, phytosterols, polyphenols, bioflavonoids and/or dietary fibre. Thus, these are all examples of suitable edible materials which may be used to prepare a nutraceutical composition.

Animal feeds, as well as most foods, generally contain one or more components selected from a carbohydrate-containing substance, a protein-containing substance, and a lipid-containing substance, so the feeds of the invention may contain one or more of these components, preferably a combination of all of these components.

Suitable starch-bearing feed/food components may for example be derived from grains, e.g. selected from the group consisting of corn, soybean, wheat, sorghum, barley, oat, and mixtures thereof. Examples of suitable starch-bearing substances include, but are not limited to, corn flour, ground corn, soybean flour, wheat flour, ground oat flour, wheat middlings, soybean meal, corn grit, and mixtures thereof.

A crude protein-bearing substance such as, for example, a fish meal, dried whey, a soybean meal, and mixture thereof can be used. Other suitable protein-bearing substances include, but are not limited to, soybean protein concentrate, soy flour, blood meal, plasma protein, dried skim milk, whey protein concentrate, canola meal, corn gluten meal, wheat gluten meal, yeast, sunflower meal, and mixtures thereof.

Suitable fat-containing substances include, but are not limited to, lard, tallow, soybean oil, lecithin, coconut oil, whey-fat blend, and mixtures thereof.

The FSY/FTY peptide of the present invention may also be formulated as a culture medium or supplement for microorganisms.

The nutraceutical composition of the present invention may contain the FSY/FTY peptide in an amount sufficient to administer to a subject suitable (i.e. effective) dosage of the FSY/FTY peptide, suitable dosages being discussed above in the context of pharmaceutical compositions.

The nutraceutical composition of the present invention may be provided as food or feed to any animal, including terrestrial and aquatic animals. The animal may be a mammal, fish, bird, vertebrate or invertebrate, e.g. seafood, livestock, pets and humans.

In a further aspect, there is provided a method of preparing a nutraceutical composition comprising an FSY/FTY peptide. Said method may comprise combining an FSY/FTY peptide with an edible material. Suitable edible materials are discussed above.

In another aspect, there is provided a method of preparing a food, drink or feed fortified with an FSY/FTY peptide. Said method may comprise combining an FSY/FTY peptide with an edible material or incorporating an FSY/FTY peptide into a food, drink or feed. Suitable foods drinks and feed are discussed above.

In another aspect, the invention provides a nucleic acid molecule encoding an FSY/FTY peptide as disclosed herein. Also provided is the complement of such a nucleic acid molecule. Preferably, the nucleic acid molecule comprises a promoter sequence and/or a transcription start site operably linked to the sequence encoding a peptide as disclosed herein and/or a transcription or translation termination sequence operably linked to the sequence encoding a peptide as disclosed herein.

The nucleic acid molecule of the invention comprises at least 9 nucleotides and preferably no more than 800 nucleotides, more preferably no more than 500, 400, 300, 200, 150, 100, 90, 80, 70, 60, 50, 45, 40, 35, 30, 25, 20 or 15 nucleotides. The nucleic acid molecule is preferably an isolated molecule. It may be a single stranded molecule, or a double stranded molecule comprising a nucleic acid strand which encodes an FSY/FTY peptide and its complement.

Transcription start codons are generally always translated into methionine (Met, M), so the nucleic acid will typically encode a peptide starting with Methionine. Thus, it may encode a peptide consisting of the sequence MFSY or MFTY and peptides comprising or consisting of these sequences are further aspects of the invention. Preferably, the initial methionine is part of a cleavable signal sequence, to allow cleavage of the peptide to release a peptide consisting of the sequence FSY or FTY.

A further aspect relates to a vector comprising a nucleic acid molecule as defined herein. The vector may also contain further elements typically found in a vector such as an origin of replication, a selectable marker such as antibiotic resistance, and/or a multiple cloning site. The vector may further be an expression vector, and may comprise further elements, e.g. transcriptional and/or translational control or regulatory elements for expression of the nucleic acid molecules. Such control elements, e.g. promoters, ribosome binding sites, enhancers, terminators etc. are well known and widely described in the art.

The vector may for example be a plasmid or a virus, preferably it is selected from a retrovirus, an adenovirus and an adenovirus-associated virus.

The nucleic acid may be used instead of or in addition to the FSY/FTY peptide in any of the aspects disclosed herein. Thus in another aspect, the invention provides a pharmaceutical composition comprising a nucleic acid molecule as defined herein and/or a vector as defined herein, together with a pharmacologically (or pharmaceutically) acceptable excipient. Uses, in particular medical uses of the nucleic acid represent further aspects of the invention.

In another aspect, there is provided a recombinant host cell containing a nucleic acid molecule and/or vector as described above. The host cell may be any prokaryotic or eukaryotic cell, bacterial and yeast cells being preferred, for example *E. coli*.

A peptide is a molecule that is formed by linking at least two amino acids, typically via an amide bond, also called a peptide bond. Thus, a peptide comprises or consists of at least 2 amino acids. Peptides consisting of two amino acids are called dipeptides, peptides consisting of three amino acids tripeptides and so on. Peptides consisting of between 2 and 20 amino acids may be referred to as oligopeptides, and peptides having less than about 50 amino acids are typically referred to as polypeptides. The term "protein" is typically used to refer to large polypeptides or complexes of polypeptides.

It should be understood that any reference made herein to an FSY/FTY "peptide" means a molecule which is present in the form of a peptide and does not include a protein which includes the recited sequence. By "present in the form of a peptide" is meant that the molecule has the size of a peptide, i.e. 2-50 amino acids, and is not an integral part of a larger entity such as a protein. Thus, the peptide may be referred to as being in "free" or "isolated" form. Thus, a composition comprising an FSY/FTY peptide is a composition in which the FSY/FTY peptide is present in the form of a peptide.

The FSY/FTY peptide and nucleic acid molecules of the invention are generally "isolated" or "purified" molecules insofar as they are distinguished from any such components that may be present in situ within a living organism such as an animal, plant, fungus or prokaryote or a sample derived from an organism. The sequences may, however, correspond to or be substantially homologous to sequences as found in an organism. Thus, the term "isolated" or "purified" as used herein in reference to nucleic acid molecules or sequences and peptides, refers to such molecules when isolated from, purified from, or substantially free of their natural environment, e.g., isolated from or purified from an organism, or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a peptide, the term "isolated" or "purified" typically refers to a peptide substantially free of cellular material or other proteins from the source from which it is derived. In some embodiments, particularly where the peptide is to be administered to humans or animals, such isolated or purified peptides are substantially free of culture medium when produced by recombinant techniques, or chemical precursors or other chemicals when chemically synthesized. Such isolated or purified peptides may also be free of flanking sequences such as those described above for the isolated nucleic acid molecules. The term "free peptide" may conveniently be used to indicate that the peptide does not form part of a protein.

The pharmaceutical compositions of the present invention can be formulated according to any of the conventional methods known in the art and widely described in the literature. Thus, the FSY/FTY peptide may be incorporated, optionally together with other active substances (examples of which are as described below), with one or more conventional pharmaceutically acceptable carriers, diluents and/or excipients, etc., appropriate for the particular use for a composition, to produce conventional preparations which are suitable or can be made suitable for administration. They may be formulated as liquids, as semi-solids or as solids, e.g. liquid solutions, dispersions, suspensions, tablets, pills, powders, sachets, cachets, elixirs, emulsions, syrups, and the like. It may be provided e.g. as a gastric fluid-resistant preparation and/or in sustained action form. It may be a form suitable for oral, parenteral, topical, rectal, genital, subcutaneous, transurethral, transdermal, intranasal, intraperitoneal, intramuscular and/or intravenous administration and/or for administration by inhalation. The preferred form depends on the intended mode of administration and therapeutic application.

In a representative embodiment, the pharmaceutical composition is in a form suitable for liposomal administration, so preferably liposomes containing the pharmaceutical composition are provided. When liposomes are used, it may not be necessary to include a further excipient, so also provided are liposomes containing an FSY/FTY peptide, a nucleic acid molecule as defined herein and/or a vector as defined herein.

The preferred mode of administration is oral. Any physiologically compatible carrier, excipient, diluent, buffer or stabilizer can be used in the compositions of the invention. Examples of suitable carriers, excipients, diluents, buffers and stabilizers include one or more of water, saline, phosphate buffered saline, dextrose, glycerol, ethanol and the like, as well as combinations thereof. In some cases isotonic agents, e.g. sugars, polyalcohols (e.g. mannitol, sorbitol), or sodium chloride may be included. The compositions may additionally include lubricating agents, wetting agents, emulsifying agents, suspending agents, preserving agents, sweetening agents, flavouring agents, and the like. The compositions of the invention may be formulated so as to provide quick, sustained or delayed release of the active ingredient after administration to the subject by employing procedures well known in the art. An enteric coating may optionally be used.

In addition to an FSY/FTY peptide, the composition may further comprise one or more further active ingredients such as other agents which are useful for treating (pre)hypertension, examples of which include ACE inhibitors, Angiotensin II receptor blockers (ARB) drugs, beta-blockers, diuretics, calcium channel blockers, alpha-blockers, and peripheral vasodilators. Preferably, the further active ingredient is a further ACE-inhibitor, which is preferably a peptide. Thus, there is provided a pharmaceutical or nutraceutical composition comprising an FSY/FTY peptide in combination with one or more further ACE-inhibitory peptides. The further ACE-inhibitory peptide may for example comprise or consist of a sequence selected from LF, FL, LY, LVK, NPK, NVY, KLP, LYK, LNA, LVAK (SEQ ID NO:1), LVAH (SEQ ID NO:2), LLTK (SEQ ID NO:3), ALPH (SEQ ID NO:4), LLLK (SEQ ID NO:5), LNPK (SEQ ID NO:6) and VLAH (SEQ ID NO:7). Preferably, at least 2, 3, 4, 5, 6, 7, 8, 9, 10, 11, 12 or 13 peptides selected from this list are present.

As set out above, the FSY/FTY peptide contains a core sequence, but it may also include one or more flanking sequences and/or include modifications. Thus, in a further aspect there is provided a composition comprising or consisting of at least 2 different FSY/FTY peptides. One or more further ACE-inhibitory peptides may also be present, as discussed above. The FSY/FTY peptides may differ from one another in their core sequence, flanking sequence(s) and/or in the modification(s). Thus, in embodiments of any of the aspects disclosed herein, two or more different FSY/FTY peptides may be present. A composition comprising a FSY peptide in combination with an FTY peptide is particularly preferred.

Suitable daily dosages may be readily determined, but for example about 1-5, e.g. about 3 mg per day may be appropriate. A typical daily dosage may depend on the weight of the subject. The skilled person will appreciate that suitable dosages may be achieved by administering a single dosage unit per day, or by administering two or more lower dosage units per day.

The pharmaceutical composition of the present invention will thus contain a suitable amount of the FSY/FTY peptide per solid dosage unit, e.g. about 3 mg per tablet, or a corresponding dosage in a liquid formulation.

In a further aspect, there is provided a method of preparing a pharmaceutical composition comprising an FSY/FTY peptide. Said method may comprise incorporating FSY/FTY peptide with a pharmaceutically acceptable carrier, diluent and/or excipient to produce a pharmaceutical composition which is suitable or can be made suitable for administration. Appropriate carrier, diluent and excipients are discussed above.

In another aspect, there is provided an in vitro method of inhibiting ACE-activity, said method comprising the use of an FSY/FTY peptide. In particular, the FSY/FTY peptide may be used to modulate the activity of ACE in a cell lysate, a cell or a tissue sample. This may provide further insights into the effects of ACE and ACE-inhibition.

Table 1 shows the results of a comparative analysis of ACE-inhibitory activity of a number of different peptides.

The invention will now be described in more detail in the following non-limited examples.

EXAMPLE 1

An FSY peptide was analysed via an enzyme assay wherein ACE produces hippuric acid (HA) from the substrate hippuryl-histidine-leucine (HHL). The HA concentration was determined by quantitative HPLC analyses and a decreased concentration was correlated with inhibitory effect. ACE-inhibitory activity was determined based on the method reported by Cushman and Cheung (1971) by measuring the end product hippuric acid (HA) from the enzymatic reaction between ACE (Sigma A 6778) and the substrate HHL (Sigma H 1635), essentially as described in Dragnes et al. J Food Composition and Analysis 2009; 22: 714-17. A 100 µl volume with 2 mM HHL in 100 mM sodium borate buffer pH 8,3 was pre-incubated at 37° C. for 30 minutes with 25 µl inhibitor (FSY peptide diluted in Sodium borate buffer). Then the assay was initiated by adding 50 µl ACE (10 mU). The enzymatic reaction was stopped by addition of 215 µl 1 M HCl.

Quantitative HPLC analyses were performed on a Shimadzu (Shimadzu Corporation, Japan), using a Symmetry-Shield reverse phase C-18 Intelligent Speed column. The HA was eluted at ambient temperature using a mobile phase that consisted of 0.05% aqueous trifluoroacetic acid and HPLC-grade acetonitrile. A 2 min linear gradient was used, beginning after 0.5 min isocratic elution with 5% acetonitrile and ending with 90% acetonitrile. The flow-rate was maintained at 2 mL min$^{-1}$ and the UV absorption was measured at 228 nm. The concentration of ACE inhibitors required to inhibit 50% of ACE activity was defined as the $IC_{50}$. The $IC_{50}$ of the FSY peptide was determined to be about 4 µM on average, with some determinations putting the $IC_{50}$ as low as 1.7 µM and typical measurements being about 2.2 µM.

When the method by Vermeirssen et al (supra) was used to determine the $IC_{50}$, values of about 7.7 µM were determined.

EXAMPLE 2

The ACE-inhibitory activity of a variant of the FSY peptide having the sequence FTY was assayed using the method described in Example 1. The $IC_{50}$ of the FTY peptide was determined to be about 59 µM using the method of Dragnes et al. (supra) and about 274 µM using the method of Vermeirssen et al (supra).

EXAMPLE 3

Determinations of $IC_{50}$ values depend on the precise assay conditions, which makes it difficult to make meaningful comparisons between $IC_{50}$ values determined in separate assays. A comparative analysis was therefore carried out to compare the ACE-inhibitory activity of the FSY peptide to known ACE-inhibitory peptides. ACE-inhibitory activity was assayed using the method of Dragnes et al. described in Example 1. The results are shown in Table 1.

TABLE 1

| Peptide | $IC_{50}$ in µg/ml | $IC_{50}$ in µM |
|---------|--------------------|-----------------|
| FSY     | 0.9                | 2.20            |
| IPP     | 1.04               | 3.20            |
| VPP     | 1.40               | 4.50            |
| VY      | 3.6                | 13.00           |

---

The invention claimed is:

1. An in vitro method of inhibiting Angiotensin Converting Enzyme (ACE)-activity comprising contacting a cell lysate, cell or tissue sample with a peptide having ACE-inhibitory activity and consisting of the sequence FSY or the sequence FTY so as to inhibit the activity of ACE in the cell lysate, cell or tissue sample.

2. A method of inhibiting ACE-activity, comprising administering to a subject having prehypertension or hypertension an ACE-inhibitory effective amount of a peptide having ACE-inhibitory activity and consisting of the sequence FSY or FTY, wherein said FSY and FTY sequences may optionally consist of one or more modifications.

3. A method according to claim 2 wherein said peptide is used to inhibit ACE-activity to treat a condition selected from coronary angina pectoris, atherosclerosis, stroke, myocardial infarction, cerebral infarction, restenosis following angioplasty, arrhythmia, tachyarrhythmia, congestive heart failure (CHF), aortic valve regurgitation, dyslipidemia, dyslipoproteinemia, diabetic nephropathy, diabetic neuropathy, microalbumia and diabetic retinopathy.

4. The method according to claim 2 wherein said one or more peptide modifications are selected from the group consisting of:
  (i) N-terminal capping;
  (ii) C-terminal capping;
  (iii) phosphorylation;
  (iv) glycosylation;
  (v) one or more amino acids in the D-configuration.

* * * * *